(12) United States Patent
Finkelstein et al.

(10) Patent No.: US 11,501,861 B2
(45) Date of Patent: *Nov. 15, 2022

(54) SYSTEM AND METHOD TO ACCESS CASUALTY HEALTH INFORMATION IN AN EMERGENCY SITUATION

(71) Applicants: David Alan Finkelstein, Boca Raton, FL (US); Paige Erin Finkelstein, Boca Raton, FL (US); Ali Simone Finkelstein, Boca Raton, FL (US)

(72) Inventors: David Alan Finkelstein, Boca Raton, FL (US); Paige Erin Finkelstein, Boca Raton, FL (US); Ali Simone Finkelstein, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/712,342

(22) Filed: Dec. 12, 2019

(65) Prior Publication Data

US 2020/0118657 A1 Apr. 16, 2020

Related U.S. Application Data

(63) Continuation-in-part of application No. 16/151,987, filed on Oct. 4, 2018, now Pat. No. 10,622,104, which is a continuation-in-part of application No. 15/293,886, filed on Oct. 14, 2016, now Pat. No. 10,140,504.

(60) Provisional application No. 62/241,232, filed on Oct. 14, 2015.

(51) Int. Cl.
*G16H 10/60* (2018.01)
*G16H 80/00* (2018.01)

(52) U.S. Cl.
CPC ............. *G16H 10/60* (2018.01); *G16H 80/00* (2018.01)

(58) Field of Classification Search
CPC ... G16H 10/60; G06F 16/583; G06F 21/6245; H04L 9/0637; H04L 9/3239; H04L 2209/88; H04L 2209/38; G06K 9/00288; G06K 9/22
See application file for complete search history.

(56) References Cited

U.S. PATENT DOCUMENTS

| | | | | |
|---|---|---|---|---|
| 2013/0035581 A1* | 2/2013 | Vesto | ...................... | G16H 10/60 600/407 |
| 2013/0060579 A1* | 3/2013 | Yu | ........................... | G06Q 10/10 705/3 |
| 2016/0321636 A1* | 11/2016 | Huh | ...................... | G06Q 20/322 |

* cited by examiner

*Primary Examiner* — Qian Yang
(74) *Attorney, Agent, or Firm* — Squire Patent Consulting & IP Law LLC; Brendan E. Squire

(57) ABSTRACT

A system, method, and computer program product for automatically identifying a casualty and matching an electronic health record (EHR) to the casualty. A casualty identification is determined by matching a presenting image of the casualty with one of a master image or a social media profile image of the casualty. A recognized patient messaging system (RPMS) is configured to query one or more electronic health records (EHR) service providers for the existence of an EHR corresponding the identified casualty and automatically communicate the existence of the EHR to the EMS provider. A blockchain trusted identification module (BTIM) is configured to establish a trust relationship between the EMS provider and the one or more EHR service providers to establish a trusted pathway for delivery of the casualty's EHR to the EMS provider. With the casualty's EHR emergency responders to can provide better care for the casualty in an emergency situation.

16 Claims, 9 Drawing Sheets

SYSTEM AND METHOD TO ACCESS CASUALTY HEALTH INFORMATION IN AN EMERGENCY SITUATION

CROSS-REFERENCE TO RELATED APPLICATION

This application is a continuation-in-part application of U.S. patent application Ser. No. 16/151,987, filed Oct. 4, 2018, which is a continuation in part application of U.S. patent application Ser. No. 15/293,866, filed Oct. 14, 2016 and claims the benefit of priority to U.S. provisional application No. 62/241,232, filed Oct. 14, 2015, the contents of which are herein incorporated by reference.

BACKGROUND OF THE INVENTION

The present invention relates to electronic health records (EHR) and, more particularly, to the determining the existence of patient EHRs for use by emergency medical services (EMS) providers.

Over one million unconscious or non-communicative patients arrive in ERs every year in the United States. Unresponsive patients pose a major hurdle for emergency first responders in need of vital information in high-stakes situations. Access to electronic health records (EHR) provides first responders with medical backgrounds, emergency contact information, and medication histories, all of which are crucial in emergency treatment. However, when the patient is unresponsive it becomes difficult or impossible to locate and obtain protected health information, or even positively identify the patient being treated.

At present, a modern solution does not exist that allow first responders to determine the existence of a patient EHR, quickly and securely obtain protected information from EHR providers when patients are unresponsive, disoriented, or poorly versed in their medical background. Current means for obtaining this information involve slow investigation and communication with a disjoint medical record network, use of expensive and invasive biometrics, or analog tools like alert bracelets.

As of 1996, the Health Insurance Portability and Accountability Act (HIPAA) established national standards for the transaction of EHRs[i]. Patients' HIPAA-protected data includes vital medical records first responders need access to at the site of emergency treatment, so a key healthcare demand entails quickly transmitting this data while maintaining patients' privacy. EHRs should be released only with the patient's permission or within the confines of law, and any information released in the context of a clinical interaction is considered confidential and must be protected[ii].

Healthcare facilities require access to this data if EHRs are to function as intended, and the key to preserving their confidentiality is to allow only authorized individuals to access this data. This requires that any relevant parties be pre-authorized to access the information based on established role-based privileges. Any user given access will be held accountable for use and misuse of the information they view, so properly assigning and validating user privileges comprises a major aspect of medical record security[iii].

Maintaining secure records has proven a rising challenge in multiple domains as increasing amounts of consumer data have become available. A 2014 report on medical identify theft in the United States suggests that incidences of data breaches are rising, with 2.32 million victims reported in 2014, a 21.7% increase from the previous year[iv]. Cloud storage, encryption, and basic password protection are vital aspects of ensuring EHRs remain secure. However, a 2011 survey found 73% of physicians confessed to texting other physicians about their work, and many healthcare professionals regularly access or discuss these records from personal mobile devices[v]. Modern devices are easily misplaced, stolen, or wrongly accessed, so modern EHR transmission and storage protocols must highlight the use of encryption and proper validation.

Likewise, because medical records play crucial roles in informing treatment, steps must be taken to ensure that EHRs are accurate and unchanged following transmission. Loss or destruction of data during transfer will raise concerns about the usability of data, making them unfit as a basis for making care decisions[vi]. Alterations to a patient's medical records may cause them to be billed for services they did not receive, misinform their caretakers, or lead them to receive unnecessary or dangerous treatments.

As can be seen, there is a need for a generalized and globally accessible system and method for (1) identifying a potentially unresponsive patient in an emergency setting, (2) locating that patient's EHRs in an unstandardized, byzantine record system, and (3) securely transmitting HIPAA-protected records from the EHR provider to the first responder at the site of treatment. improving the identification of a casualty at an injury or incident site, or on presenting at an Emergency services health care facility on an initial encounter with that facility.

SUMMARY OF THE INVENTION

In some aspects of the invention, a system for automatically determining the existence of an electronic health record corresponding to an identified casualty across one or more electronic health records (EHR) providers is disclosed. The system includes a server hosting a casualty identification and EHR matching service. The server includes a patient identification module configured to identify a casualty based on an identification of the casualty received from a mobile computing device operated by an emergency medical services (EMS) provider. A recognized patient messaging system (RPMS) is configured to query one or more electronic health records (EHR) service providers for the existence of a corresponding EHR belonging to the identified casualty upon receipt of the identification.

The Recognized Patient Messaging System (RPMS) protocol utilizes webhooks that upon receipt of the identification, deliver data to initiate a query, or a request, to a server of the one or more EHR service providers.

A database repository contains a plurality of EHR records. The database repository is affiliated with the one or more EHR service providers. Responsive to the one or more webhooks, the one or more servers of the EHR service providers initiate a query of the database repository to determine the existence the corresponding EHR. The one or more webhooks include a patient identifier corresponding tor the identified casualty.

An application program interface (API) on the server hosting the casualty identification and EHR matching service is configured to receive a POST request from the server of the one or more EHR service providers. The POST request provides an indication of the existence of the corresponding EHR. When a corresponding EHR exists, the POST request provides information to request the corresponding EHR from a custodian of the EHR. When a corresponding EHR does not exist, the POST request returns a null result.

Other aspects of the invention include a computer program product stored on a non-transitory computer storage medium comprising machine-readable program code for causing, when executed, a computer to perform process steps. The process steps include receiving an identification of a casualty, at a first server hosting a casualty identification and electronic health record (EHR) matching service. Responsive to receiving the identification, the first server automatically queries a second server hosted by one or more electronic health record (EHR) service providers to determine the existence of a corresponding EHR matching the casualty.

The automatic query may include generating one or more webhooks by the first server upon receipt of the identification. The one or more webhooks are distributed to the second server, and include a user defined callback to communicate one or more of a push notification, a query, or a request, to the second server to determine the existence of the corresponding EHR. The webhook notifies a webhook listening service, set up by the EHR to query their respective databases to determine the existence the corresponding EHR.

The process steps may also include, the EHR service sending a POST request corresponding to the first server's application program interface (API) endpoint. The POST request provides an indication of the existence of the corresponding EHR. When a corresponding EHR exists, the POST request includes relevant contact information to request the corresponding EHR from a custodian of the EHR. When a corresponding EHR does not exist, the POST request returns a null result.

Yet other aspects of the invention include a method of automatically matching an electronic health record (EHR) to an identified casualty. The method includes receiving an identification of a casualty at a first server hosting a casualty identification and electronic health record (EHR) matching service. Upon receipt of the identification, a second server hosted by one or more electronic health record (EHR) service providers are automatically queried to determine the existence of a corresponding EHR matching the casualty. When the corresponding EHR is located, the method automatically transmits a notification of the existence of the corresponding EHR to a mobile computing device of a medical provider treating the casualty.

In some embodiments, the step of automatically querying includes distributing one or more webhooks by the first server upon receipt of the identification. Via the webhook, the information is transmitted to the second server. The webhook broadcasts comprising a user defined callback to communicate one or more of a push notification, a query, or a request, to the second server to determine the existence of the corresponding EHR. Responsive to receipt of the one or more webhooks, a database repository affiliated with the one or more EHR service providers is automatically queried to determine the existence the corresponding EHR.

In some embodiments of the method, a POST request is received at an application program interface (API) of the first server from the second server. The POST request providing an indication of the existence of the corresponding EHR. When a corresponding EHR exists, the POST request provides contact information to request the corresponding EHR from a custodian of the EHR. When the corresponding EHR does not exist, the POST request returns a null result.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention, hereinafter ERinfo, provides an improved platform with the ability to determine the existence of an EHR from one or more cooperating EHR service providers to determine the availability of an EHR for an identified patient. If relevant EHRs are found, the EHR provider can return a response indicating the location of the EHR.

Figure 1:
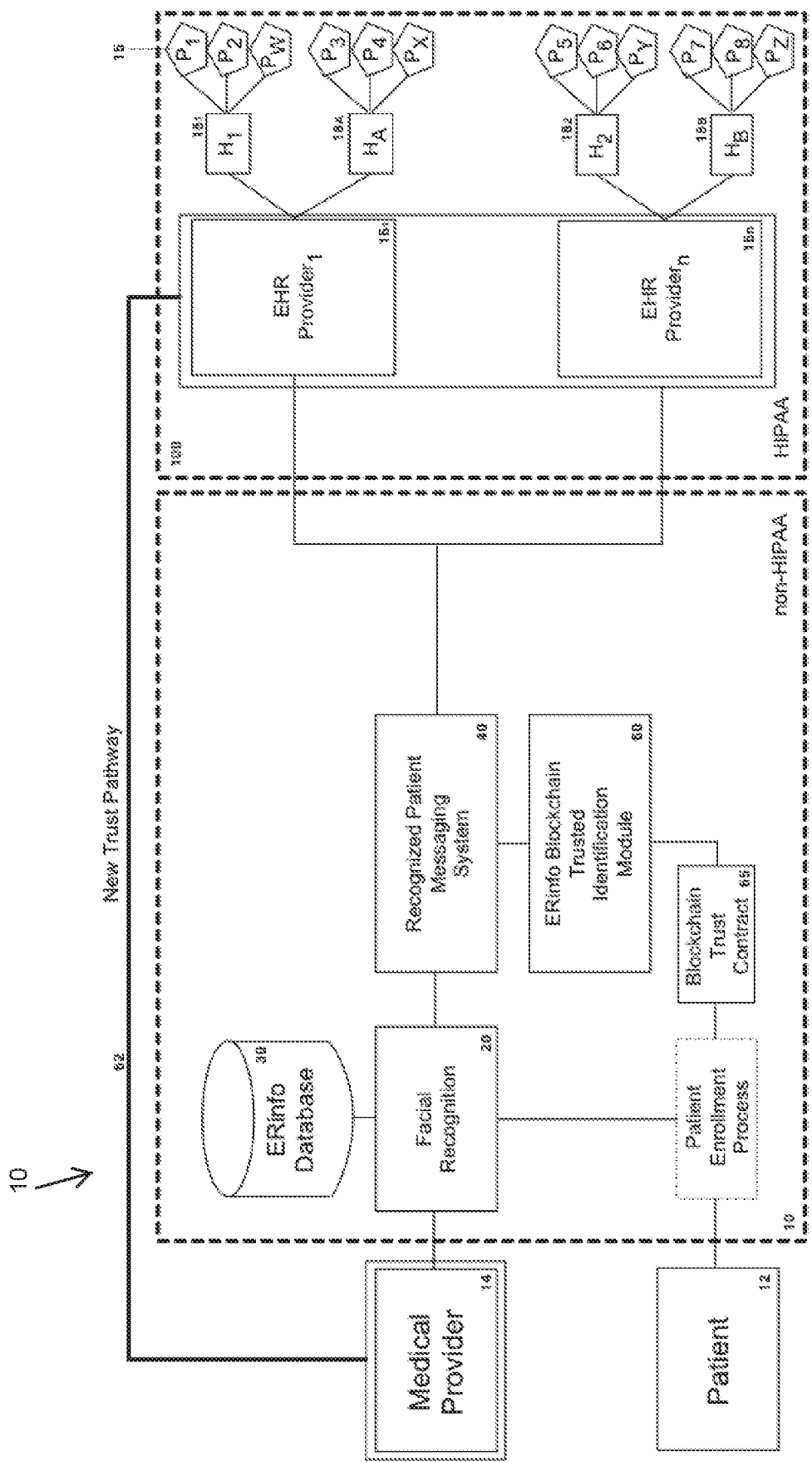
FIG. 1 illustrates a representative system architecture for the ERinfo platform.
Figure 2:
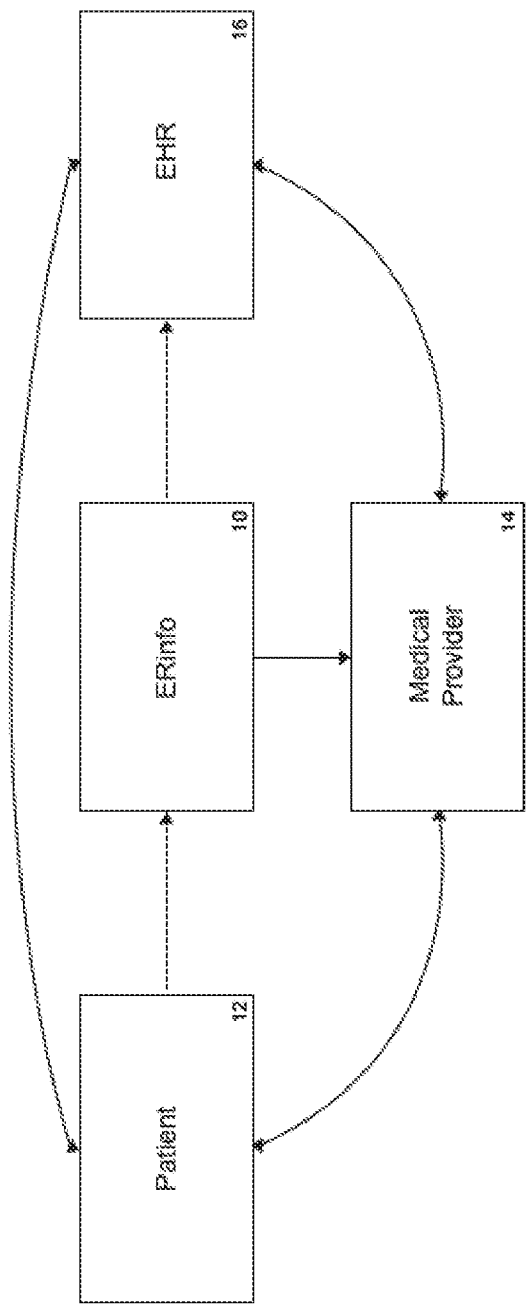
FIG. 2 illustrates trust relationships of the ERinfo platform.

As seen in reference to FIG. 1, the ERinfo platform 10 may include three integral modules as part of the trust pathway, each addressing one of the needs in secure EHR access: (1) a patient identification module 20, which may include a facial recognition module, (2) a recognized patient messaging system (RPMS) 40, and (3) a blockchain trusted identification module 60. The three modules acting in concert may allow near-instantaneous and secure access to the casualty's protected health information from the authorized medical provider's smart phone 13, or other mobile computing device.

Once a casualty's identity has been determined, the ERInfo's platform 10 may provide healthcare professionals 14 with an indication of the existence of EHRs 15 maintained by one or more EHR providers 16, ultimately allowing access to vital records on site. First responders and emergency physicians 14 will be able to begin targeted treatment and contact relevant individuals and providers significantly faster, lessening unnecessary diagnostic tests and expenses while facilitating vital EHR 15 communication. The platform 10 addresses the challenge of matching an identified patient with an existing EHR 15 that may be kept by one or more EHR providers 16.

The ERinfo platform 10 provides a timely and secure system applicable to many contingencies, including but not limited to: a) patients who are disoriented or unresponsive due to trauma or medical emergency; b) Individuals non-compliant due to alcohol or drug overuse; c) "Silver Alerts" when patients with Alzheimer's or dementia become lost or disoriented; d) Natural disasters & mass casualties, in which high volumes of patients must be identified under high-stress, chaotic circumstances; and d) patients with low medical literacy regarding their healthcare background and risk factors.

As seen in reference to FIG. 1, once a patient 12 has been identified, the recognized patient messaging system (RPMS) 40 will push queries to one or more cooperating EHR service providers $16_1$-$16_n$ to determine the availability of an EHR 15 for the identified patient 12. If relevant EHRs 15 are found, the EHR provider $16_1$-$16_n$ will return a response indicating the location of the EHR records 15. If relevant EHRs 15 are not found, the system 10 notifies the first responder 14 of the absence of an existing EHR so that time is not spent waiting on a result that won't be forthcoming.

The recognized patient messaging system 40 (RPMS) is responsible for the determination of the existence of and a location of a recognized patient's medical records 15. Once a patient has been identified by the presenting image or any other identification means, the RPMS 40 will push a query to one or more EHR providers 16 in order to determine which EHR provider $16_1$-$16_n$ may have the identified patient's records in their system. The query may be based on relevant patient demographic information that may be captured during the matching of the presenting image to the source providing the matching identity for the patient, or patient demographic information obtained from the patient, and one or more other sources. By way of non-limiting example, the query may include: First Name, Last Name, Address, SSN, a Medical Health Insurance number, a Medical Health Record number, Date of birth, etc.

If one of the EHR providers $16_1$-$16_n$ identifies the patient's information in their system, through one or more of their participating hospitals 18, healthcare providers, clinics, and the like, they will return a response to the RPMS 40 indicating that one or more EHR records 15 are available for the identified patient 12.

The RPMS 40 connects ERinfo in real time to the various EHR providers $16_1$-$16_n$. In some embodiments, the one or more EHR providers $16_1$-$16_n$ may implement a listening module configured to autonomously receive the RPMS 40 push notifications.

ERinfo 10 runs a service or services on its servers that broadcast the query containing the patient's identifying information matched to any and all EHR providers $16_1$-$16_n$ that are running a listening service that may be implemented using ERInfo's RPMS software development kit and proprietary APIs for the one or more EHR providers 16. In the alternative, should a third party listener be made available that can accept broadcast messages from ERinfo's RPMS 40, the third party listener can be used as well by the one or more EHR providers $16_1$-$16_n$.

The ERinfo listening service running on the one or more EHR provider $16_1$-$16_n$ servers may also configured to transmit a response from the one or more EHR providers $16_1$-$16_n$ that are responding to the query for the existence of a corresponding EHR 15 for the patient 12 within their system. When the ERinfo platform 10 receives a response, the system may be configured to transmit the existence and location of the patient's EHR 15 to the medical provider 14.

Figure 8:
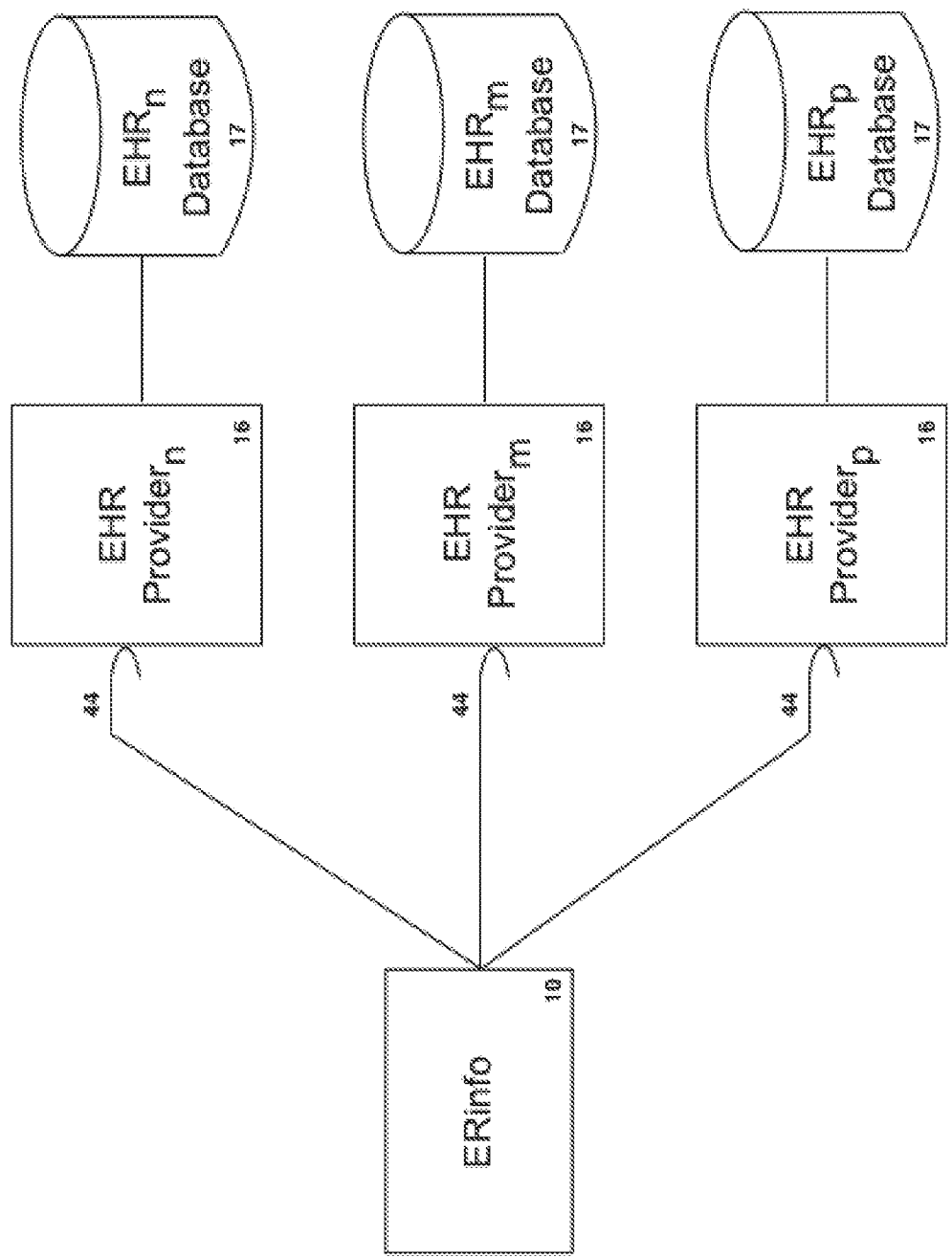
FIG. 8 illustrates a diagram illustrating implementation of a Recognized Patient Messaging System (RPMS) protocol.

In a preferred embodiment, communication between the RPMS 40 and EHR companies $16_1$-$16_n$ is executed utilizing an ERinfo Recognized Patient Messaging System (RPMS) protocol 42. The RPMS protocol 42 takes advantage of one or more webhooks 44—user defined HTTP callbacks that send out push notifications, queries, or requests via HTTP POST requests upon predetermined mutations and occurrences, such as receipt of the patient identification. As seen in reference to FIGS. 8 and 9, utilizing these in combination with one or more API calls, the ERinfo RPMS 45 protocol is executed as follows:

Upon recognition of a patient 12, whether through the facial recognition query, or otherwise, an ERinfo RPMS webhook trigger 45 is issued, announcing the request for the identified patient's information. The webhook 44 transmits a patient identifier 46.

The one or more participating EHR companies $16_1$-$16_n$ following the ERinfo RPMS protocol 42 will be notified of the new query.

The one or more participating EHR companies $16_1$-$16_n$ will execute an internal query of their database 17 to determine if the identified patient 12 is present in their system. This internal query will check for the existence of patient records 15 in the one or more hospitals or providers $18_n$ utilizing their EHR system $16_n$. If an EHR 15 corresponding to the identified patient 12 is found, the EHR company $16_n$ servers will execute an HTTP POST request 46 to an ERinfo API containing relevant information pertaining to the existence of thee record and contact information to obtain that record 15. If an EHR 15 is not found, the HTTP Post request 46 return null result.

Figure 3:
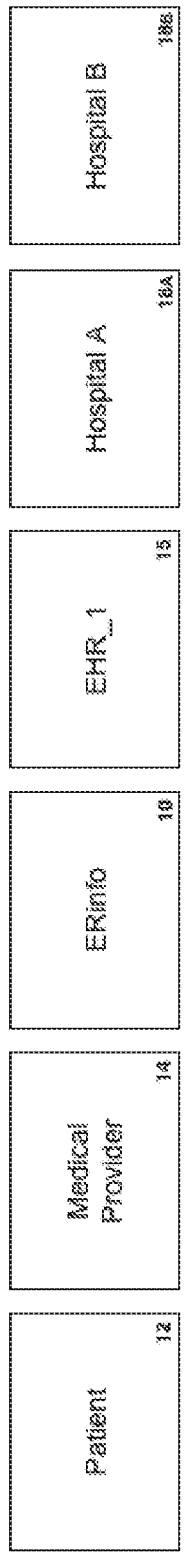
FIG. 3 illustrates participating parties in the exchange of patient information within the ERInfo platform.
Figure 9:
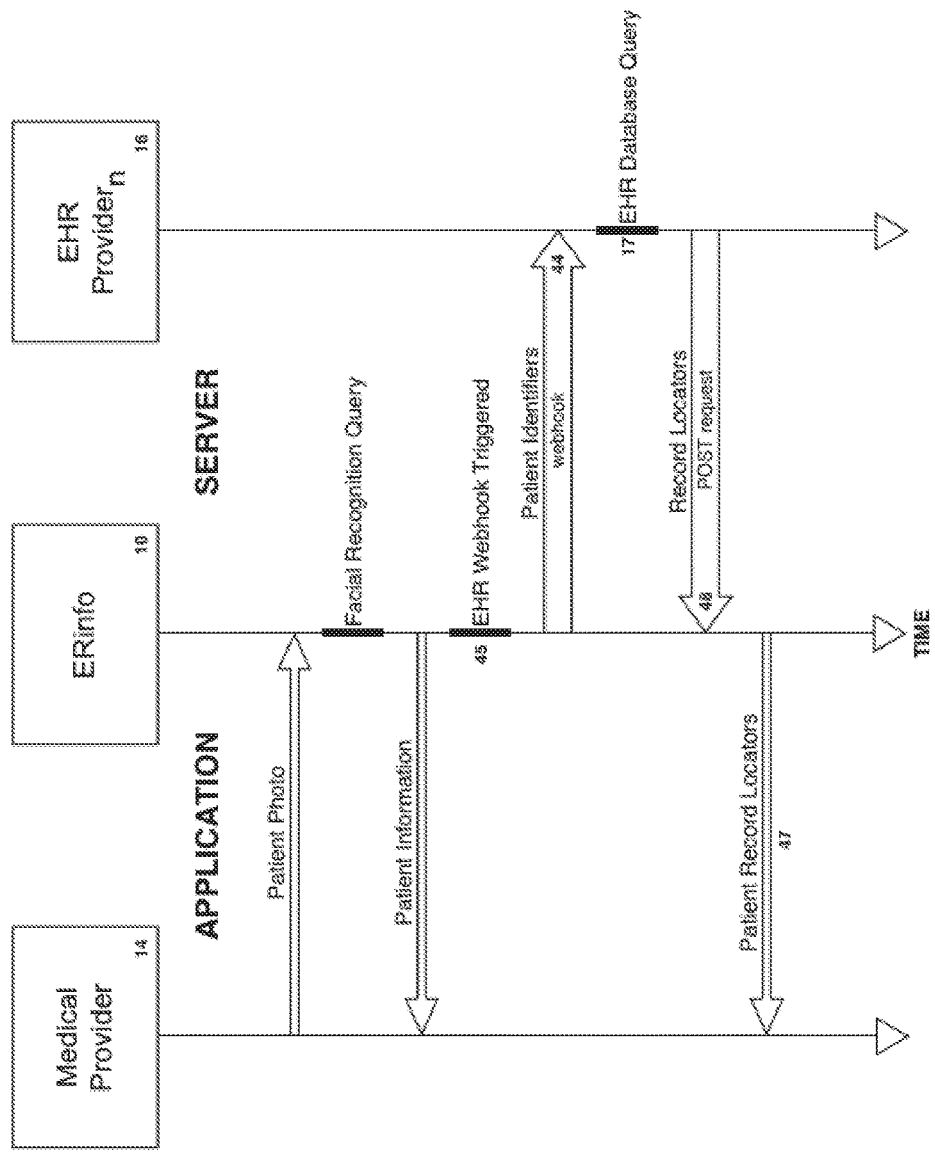
FIG. 9 illustrates a timing and sequencing of the RPMS protocol.
Figure 10:
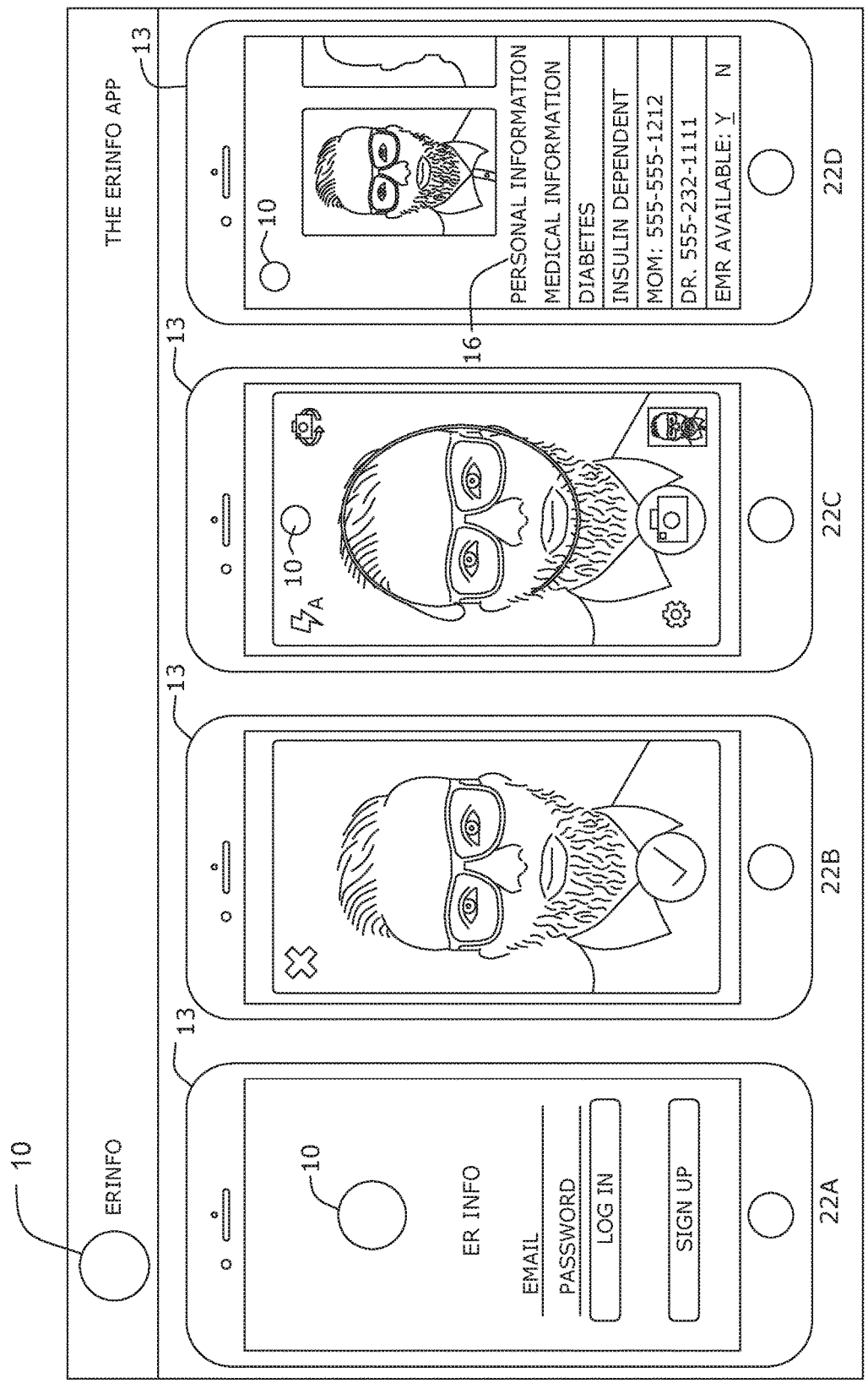
FIG. 10 illustrates a user interface for obtaining an identity of a casualty from a facial recognition module.
Figure 11:
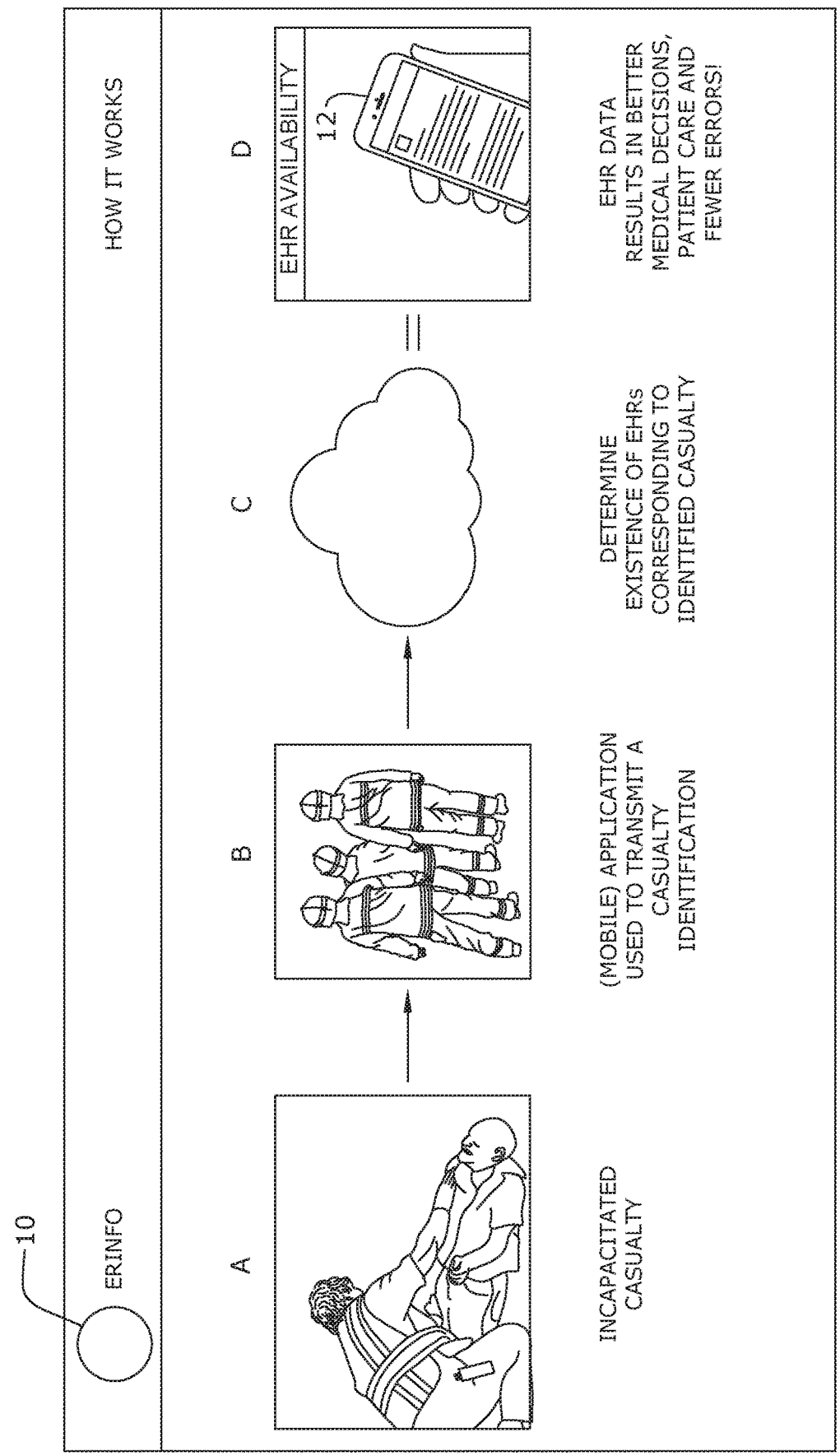
FIG. 11 illustrates a schematic diagram for a representative use of the RPMS to obtain a casualty EHR information.

As seen in reference to FIG. 9, a timeline of the ERinfo RPMS protocol 42 and its location in the ERinfo identification protocol 40 is demonstrated in FIG. 3. The ERinfo RPMS webhook 44 may be distributed to the one or more participating EHR companies $16_1$-$16_n$ and integrated into their respective servers and systems accordingly.

Upon determining a casualty identity, a webhook trigger 45 is issued by the ERInfo server 10 to the one or more EHR companies $16_1$-$16_n$. The webhook trigger 45 includes one or more patient identifiers 46. Responsive to the trigger 45, the one or more EHR companies $16_1$-$16_n$ execute a query of the database 17 of their participating healthcare providers 18 for one or more EHR records 15 corresponding to the one or more patient identifiers 46.

Upon completion of the query, the servers of the one or more EHR companies $16_1$-$16_n$ transmit a response to ERInfo 10. A return POST request 48 will contain a record locator 47 including the generic contact information, e.g. phone number to call in order, for a custodian of the EHR 15, that will allow the first responder 14 to request access to the EHR 15. In this instance, while the medical provider 14 has awareness of the existence and location of the patient's corresponding EHR 15, a direct link to the patient's corresponding EHR is not provided, and the record 15 may be retrieved utilizing conventional means, in a protected manner. As will be appreciated, the RPMS protocol 42 doesn't convey protected health information, rather it provides the medical provider 14 awareness of the existence of the corresponding EHR for the patient 12. The record locators 47 allow the medical provider 14 the ability to contact the record custodian and obtain the relevant EHR 15. In the event the medical provider 14, patient 12, and EHR provider 16 are all participants of the same private ledger blockchain trust, the ERinfo platform 10 provides for the EHR provider 16 to forward authentication and access credentials to the medical provider 14 so that the medical provider 14 can directly access the patient's protected health information 15 that is resident on one or more of the EHR provider's systems 16 via a blockchain trusted identification module (BTIM) 60.

The BTIM 60 establishes a consensus and a trustworthiness of the EHR provider $16_1$-$16_n$ and the first responder 14, ensuring secure transfer of EHR documents 15 directly to the first responder 14 via the trust pathway 62. Once complete, the three modules acting in concert will allow near-instantaneous and secure access of protected information from the authorized medical provider's phone.

The Trust Pathway 62 addresses the two major hurdles to obtaining vital EHRs 15 in emergency situations by employing innovative models within the central ERinfo platform 10: Messaging via the recognized patient messaging system 40, and EHR 15 delivery through the BTIM 60. The modules may be operated sequentially to authorize secure transmission of EHRs. 15.

Figure 4:
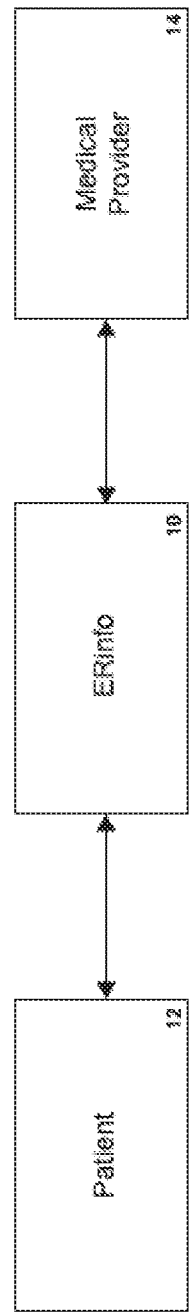
FIG. 4 illustrates trust exchanges within the ERInfo platform via smart contracts.

When the RPMS 40 receives the notification, the blockchain trusted identification module (BTIM) 60 is responsible for establishing the secure retrieval of HIPAA-protected information using a blockchain enabled trust pathway 62. As seen in reference to FIG. 3, all parties involved, including first responders 14, EHR service providers 16, and patients 12 who have opted into ERInfo functionality, will execute a smart contract with ERInfo 10 establishing a consensus on accessibility and sharing of the EHR 15 and other vital patient information. For an enrolled patient 12, as seen in reference to FIG. 4, because the patient 12 has signed a smart contract to establish a trust pathway with ERInfo 10, and ERInfo 10 has created a smart contract with the one or more EHR providers 16, the patient's EHR 15 can be released to the requesting provider 14 at the site of treatment.

Figure 5:
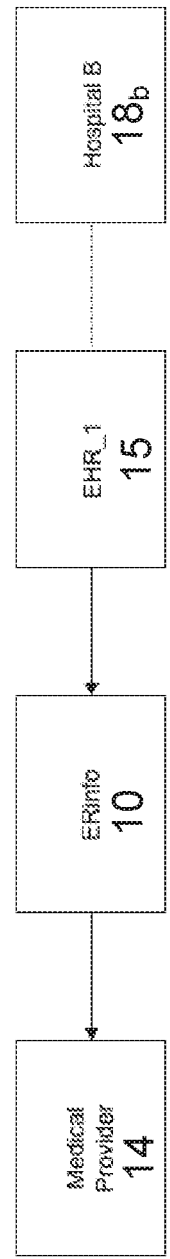
FIG. 5 illustrates a representation of a flow of trust within the ERInfo platform.
Figure 6:
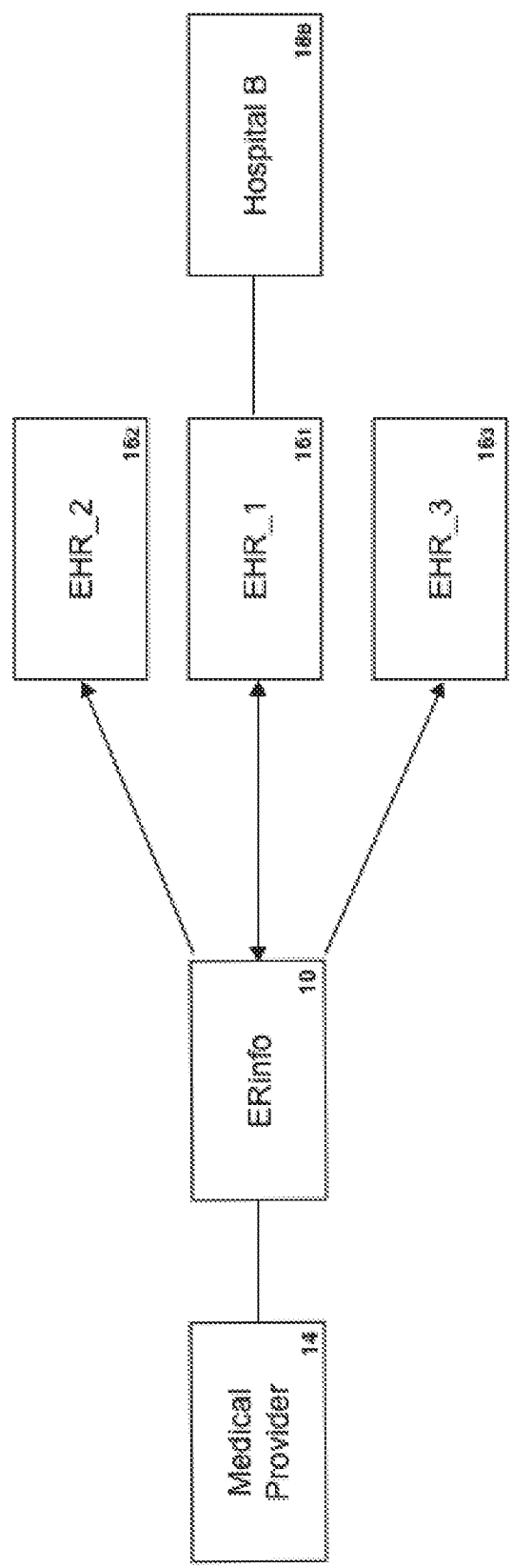
FIG. 6 illustrates a recognized patient EHR query provided through the ERInfo platform.
Figure 7:
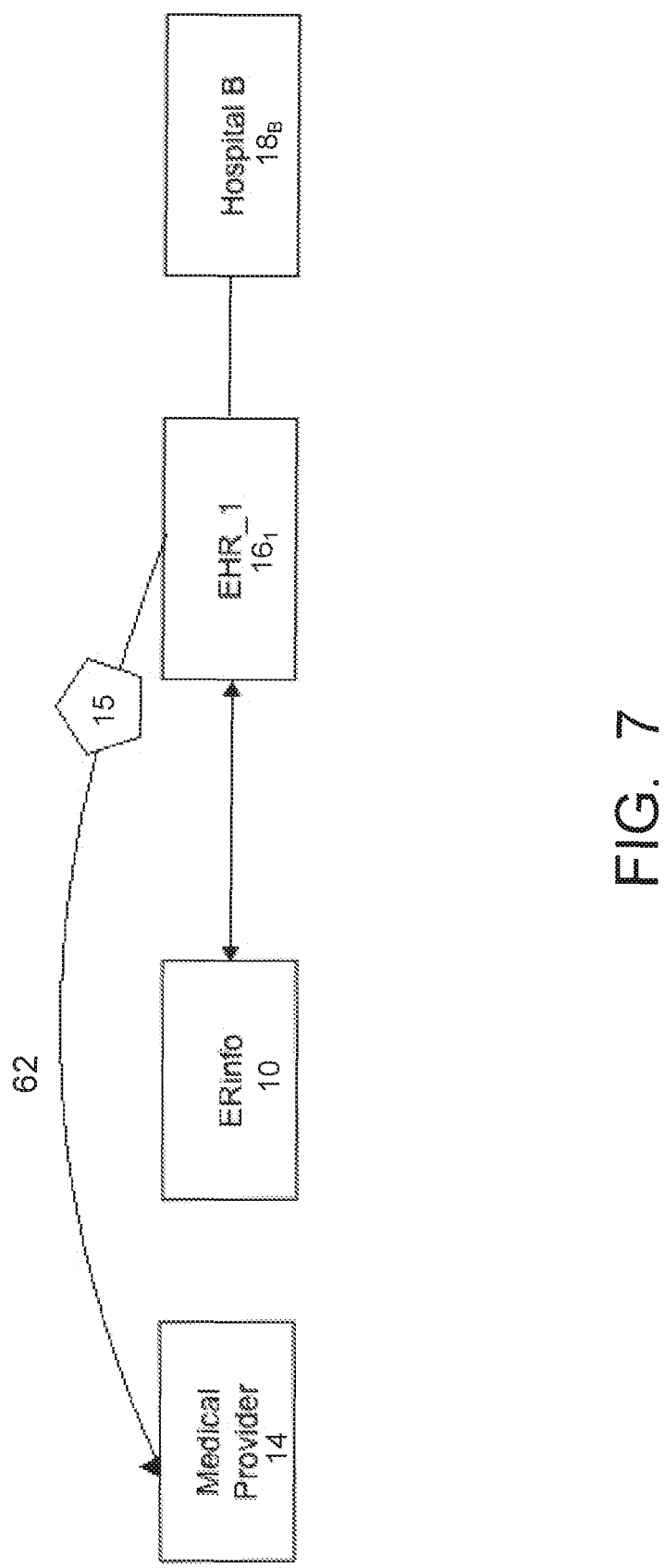
FIG. 7 illustrates delivery of an EHR to the requesting provider.

In the case of a non-enrolled patient 12, when the provider 14 verifies an emergency condition exemption, a trust pathway 62 with ERInfo 10 and the EHR provider 10 is executed, as illustrated in reference to FIG. 5, enabling the release of the one or more EHRs to the requesting provider 14. In either case, the trusted pathway 62 is configured so that the patients one or more EHRs 15 are delivered directly to the requesting provider 14 so that the ERInfo platform 10 need not be HIPAA compliant.

Using the blockchain-protected system in which a plurality of participants are consensus providers ensures that no single party can serve as a vulnerable endpoint for accessing sensitive patient information; there must be consensus among all members of the decentralized ledger to verify a valid EHR 15 request. This ensures that only actively licensed (and authorized through ERInfo platform 10) providers 14 can access the system, and that a security breach of the ERInfo database 30 itself does not allow intruder access to HIPAA data of patients 12 who have opted in.

Once the patient has been recognized and their EHRs located, the blockchain trusted Identification module 60 validates and automatically executes the one or more smart contracts, thereby permitting the EHR provider 16 to deliver the identified patient's EHRs 15 to the first responder or medical provider 14. The one or more smart contracts may include a smart contract that a medical provider 14 enters into with ERinfo 10 when enrolling with ERinfo 10. The one or more smart contracts may also include a smart contract between ERinfo 10 and the one or more EHR providers 16. In turn, the EHR provider 16 may require an additional contract with each facility/organization 18 using its system, the additional contract may also be a smart contract. The one or more smart contracts may also include a smart contract between the patient 12 and ERinfo 10.

The ERinfo platform 10 uses a distributed application (DApp) to establish transitive trust through enrollment with the system 10. The DApp manages separate enrollment for the patient 12, the medical provider 14, and the EHR service provider 16 through one or more smart contracts: When an EHR service provider 16 is enrolled, the one or more smart contracts on a blockchain system, when executed, will provide previously unauthorized first responders 14 to seamless access to the patient's EHR information 15 by the EHR service provider 16. The ERinfo platform 10 creates transitive trust with the DApp managing enrollment, the Patient's smart contract for a record release can be automatically executed using ERInfo's established trust across all parties. Trust can be then be established between the EHR provider 16 and the medical provider 14. The EHR provider 16 can then provide access to the patient's record 15 with trust and release the relevant information.

Patient Enrollment. When a patient 12 enrolls with ERInfo 10, the patient 12 can provide ERinfo 10 with appropriate and legally acceptable permission, a smart contract, to retrieve their (HIPAA) protected medical information 15. With the patient's smart contract on the blockchain, previously unauthorized first responders 14 are granted access to the patient's information 15 in the event of an emergency and execution of the patient's smart contract.

The "trust" relationship is created by ERinfo 10, where the patient 12 can rely on ERinfo 10 to ensure that only properly authorized medical professionals 14 and first responders 14 can access their information, and that institutions 16, 18 that are part of ERInfo's blockchain can publish that information 15 to those digitally authenticated medical providers 14.

Medical Provider Enrollment. When a medical provider 14 enrolls as an ERinfo provider, ERinfo 10 validates the enrollment using credentialing services to ensure the user holds an active professional license. User validation may be provided via knowledge based authentication (KBA) or other authentication methodologies.

Thus, ERinfo 10 provides a blockchain-enabled Trust Pathway 62 authorizing the exchange of HIPAA-protected records 15. Because authorization will depend on the addition of new transactions to a distributed ledger, implementation of the system architecture is based on an established consensus between the parties involved in the transactions. This consensus can be established by a system of transitive trust conducted through members enrolled in the ERinfo service 10.

The system of the present invention may include at least one computer with a user interface. The computer may include any computer including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the software via the web browser using the internet, extranet, intranet, host server, internet cloud and the like.

The computer-based data processing system and method described above is for purposes of example only, and may be implemented in any type of computer system or programming or processing environment, or in a computer program, alone or in conjunction with hardware. The present invention may also be implemented in software stored on a non-transitory computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A system for automatically determining an existence of an electronic health record corresponding to an identified casualty across one or more electronic health records (EHR) service providers, comprising:
    a server hosting a casualty identification and EHR matching service, the server comprising:
        a patient identification module configured to identify a casualty based on an identification of the casualty received from a mobile computing device operated by an emergency medical services (EMS) provider; and
        a recognized patient messaging system (RPMS) configured to query one or more electronic health records (EHR) service providers running a listening service, for the existence of a corresponding EHR belonging to the identified casualty upon receipt of the identification, the RPMS configured to utilize a webhook, that, upon receipt of the identification, broadcasts a notification to each of the one or more EHR service providers, broadcasting a user defined callback to communicate one or more of a push notification, a query, or a request, to a server of each of the one or more EHR service providers.

2. The system of claim 1, further comprising:
    a database repository containing a plurality of EHR records, the database repository affiliated with the one or more EHR service providers; wherein, responsive to the webhook, the one or more servers of the EHR service providers initiate a query of the database repository to determine the existence the corresponding EHR.

3. The system of claim 2, wherein the webhook broadcasts a patient identifier corresponding tor the identified casualty.

4. The system of claim 1, further comprising:
    an application program interface (API) on the server hosting the casualty identification and EHR matching service configured to receive a POST request from the server of the one or more EHR service providers, the POST request providing an indication of the existence of the corresponding EHR.

5. The system of claim 4, wherein when a corresponding EHR exists, the POST request provides information to request the corresponding EHR from a custodian of the EHR.

6. The system of claim 4, wherein when a corresponding EHR does not exist, the POST request returns a null result.

7. A computer program product stored on a non-transitory computer storage medium comprising machine-readable program code for causing, when executed, a computer to perform the following process steps:
    receiving an identification of a casualty, at a first server hosting a casualty identification and electronic health record (EHR) matching service;
    broadcasting a webhook by the first server to a webhook listening service operating on a second server, the webhook listening service comprising a user defined callback to communicate one or more of a push notification, a query, or a request, to the second server to determine an existence of a corresponding EHR;
    automatically querying the second server hosted by one or more electronic health record (EHR) service providers to determine an existence of a corresponding EHR matching the casualty; and
    when an EHR is located, automatically transmitting a notification of the existence of the corresponding EHR to a mobile computing device of a medical provider treating the casualty.

8. The computer program product of claim 7, wherein the webhook is configured to automatically querying a database repository affiliated with the one or more EHR service providers to determine the existence the corresponding EHR.

9. The computer program product of claim 8, wherein the webhook includes a patient identifier corresponding tor the casualty.

10. The computer program product of claim 9, further comprising:
    receiving a POST request at an application program interface (API) of the first server from the second server, the POST request providing an indication of the existence of the corresponding EHR.

11. The computer program product of claim 10, wherein when a corresponding EHR exists, the POST request provides contact information to request the corresponding EHR from a custodian of the EHR.

12. The computer program product of claim 11, wherein when a corresponding EHR does not exist, the POST request returns a null result.

13. A method of automatically matching an electronic health record (EHR) to an identified casualty, comprising:
    receiving an identification of a casualty, at a first server hosting a casualty identification and electronic health record (EHR) matching service;
    triggering a webhook on the first server upon receipt of the identification,
    broadcasting a notification to a webhook listening service operating on a second server for each of a plurality of EHR service providers via the webhook,
    receiving the identification at a webhook listening service operating on the second server;
    automatically querying the second server hosted by one or more electronic health record (EHR) service providers to determine an existence of a corresponding EHR matching the casualty; and
    when an EHR is located, automatically transmitting a notification of the existence of the corresponding EHR to a mobile computing device of a medical provider treating the casualty.

14. The method of claim 13, further comprising:
responsive to receipt of the notification, automatically querying a database repository affiliated with the one or more EHR service providers to determine the existence the corresponding EHR.

15. The method of claim 14, further comprising:
receiving a POST request from the second server at an application program interface (API) of the first server, the POST request providing an indication of the existence of the corresponding EHR.

16. The method of claim 14, wherein when a corresponding EHR exists, a POST request provides contact information to request the corresponding EHR from a custodian of the EHR; and when the corresponding EHR does not exist, the POST request returns a null result.

\* \* \* \* \*